(12) United States Patent
Thomson et al.

(10) Patent No.: US 10,592,581 B2
(45) Date of Patent: Mar. 17, 2020

(54) METHOD FOR INVERSE TRAJECTORY PLANNING

(71) Applicant: Brainlab AG, Munich (DE)

(72) Inventors: Rowena Thomson, Kirchheim (DE); Stephan Mittermeyer, Landshut (DE)

(73) Assignee: Brainlab AG, Munich (DE)

( * ) Notice: Subject to any disclaimer, the term of this patent is extended or adjusted under 35 U.S.C. 154(b) by 1451 days.

(21) Appl. No.: 14/417,929

(22) PCT Filed: Jan. 29, 2013

(86) PCT No.: PCT/EP2013/051630
§ 371 (c)(1),
(2) Date: Jan. 28, 2015

(87) PCT Pub. No.: WO2014/019714
PCT Pub. Date: Feb. 6, 2014

(65) Prior Publication Data
US 2015/0302166 A1    Oct. 22, 2015

(30) Foreign Application Priority Data

Jul. 30, 2012    (WO) ................. PCT/EP2012/003234

(51) Int. Cl.
*G06F 17/10*    (2006.01)
*G06F 19/00*    (2018.01)
*G16H 50/50*    (2018.01)

(52) U.S. Cl.
CPC ............ *G06F 17/10* (2013.01); *G06F 19/321* (2013.01); *G06F 19/3481* (2013.01); *G16H 50/50* (2018.01)

(58) Field of Classification Search
CPC .. G06F 19/3437; G06F 19/3481; G06F 17/10; G06F 19/321; G16H 50/50;
(Continued)

(56) References Cited

U.S. PATENT DOCUMENTS

2009/0259230 A1 * 10/2009 Khadem ............ A61B 19/5244
606/130

FOREIGN PATENT DOCUMENTS

WO    WO 9942977 A1 *  8/1999 ............... G06T 7/13

* cited by examiner

*Primary Examiner* — Boniface N Nganga
(74) *Attorney, Agent, or Firm* — Tucker Ellis LLP (57) ABSTRACT

The present invention relates to a data processing method of determining a trajectory of a medical instrument to be inserted into a patient's body for treatment of a target region in the patient's body, the method being executed by a computer and comprising the following steps:
   a) acquiring medical image data comprising medical image information describing an image of an anatomical body part;
   b) acquiring target region extent data comprising target region extent information describing a spatial extent of the target region in the medical image information;
   c) determining, based on the target region extent data, whether the spatial extent of the target region in the medical image information comprises more than one image particle;
   d) if it is determined that the target region comprises more than a predetermined number of image particles, determining, based on the medical image data, image particle weight data comprising image particle weight information describing a weight describing a tissue type component of the target region assigned to each target region image particle in the target region, which component is represented at least partly by the image particle, and determining, based on the image particle weight data and the medical image data, instrument trajectory data comprising instrument trajectory infor-
(Continued)

mation describing a trajectory of the medical instrument along which the instrument is to be inserted into the patient's body.

11 Claims, 1 Drawing Sheet

(58) Field of Classification Search
CPC ........ G16H 30/63; G16H 30/00; A61B 34/10; A61B 34/20; A61B 6/032; A61B 5/745; G09B 23/30; G09B 23/28; G09B 2034/107

See application file for complete search history.

METHOD FOR INVERSE TRAJECTORY PLANNING

RELATED APPLICATION DATA

This application is a national phase application of International Application No. PCT/EP2013/051630 filed Jan. 29, 2013 and published in the English language which claims priorty to PCT/EP2012/003234 filed Jul. 30, 2012.

The present invention is directed to a method, in particular data processing method, of determining a trajectory of a medical instrument to be inserted into a patient's body in accordance with claim 1, a corresponding computer program, computer executing the program and program storage medium storing the program as well as a signal wave carrying information representing the program. Furthermore, the invention is directed to a system, in particular navigation system, for an image-guided medical procedure, the system comprising the aforementioned computer.

In medical procedures such as drug-based tumour therapy or application of contrast agents, a medical instrument, in particular a catheter such as a syringe needle or a tube line, is inserted into a patient's body to a desired location at which a medical substance, which preferably is fluid and in particular comprises a drug and/or a contrast agent, is to be infused. The medical instrument has to be lead along a trajectory, i.e. a path along which it is to be inserted, which preferably shall have a predetermined distance from and in particular shall not cross certain risk objects such as organs at risk or other off-target regions. When treating tumours in the central nervous system, trajectory planning may help to avoid adverse effects or neurological deficits which may be caused by a medical instrument crossing such risk objects for example in the brain. Currently, trajectories are planned by using anatomical landmarks and/or medical imaging methods like certain MRI modalities.

Trajectory planning usually involves following several predetermined conditions that the user must consider in parallel. These conditions are in general visualized in existing planning software to support the user in complying with the conditions associated with the envisaged medical procedure. However, even with visualization, trajectory planning can be time-consuming. Furthermore, it is challenging for a user to satisfy several conditions within three-dimensional space when viewing two-dimensional images.

A problem to be solved by the present invention thus is to increase the efficiency and reliability of planning a trajectory of a medical instrument inside a patient's body.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The invention in particular provides a method which allows for automatic or semi-automatic trajectory planning that can be run in a processor-based setting, in particular on a computer, preferably without user interaction at least during the initial planning stages.

In the following, specific terminology shall be defined which is used throughout the present disclosure.

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. However, some of the changes in the anatomical structure, in particular the pathological changes in the structures (tissue), may not be detectable and in particular may not be visible in the images generated by the imaging methods. A tumour for example represents an example of a change in an anatomical structure. If the tumour grows, it may then be said to represent an expanded anatomical structure. This expanded anatomical structure may not be detectable; in particular, only a part of the expanded anatomical structure may be detectable. Primary/ high-grade brain tumours are for example usually visible on MRI scans when contrast agents are used to infiltrate the tumour. The MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernable in the image generated by the imaging method. In addition to these tumours, referred to as "enhancing" tumours, it is thought that approximately 10% of brain tumours are not discernable on a scan and are in particular not visible to a user looking at the images generated by the imaging method.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention is also directed to a navigation system for computer-assisted surgery. This navigation system preferably comprises the aforementioned computer for processing the data provided in accordance with the data processing method as described in any one of the preceding embodiments. The navigation system preferably comprises a detection device for detecting the position of the detection points which represent the main points and auxiliary points, in order to generate detection signals and to supply the generated detection signals to the computer such that the computer can determine the absolute main point data and absolute auxiliary point data on the basis of the detection signals received. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a monitor or a loudspeaker. The user interface can use any kind of indication signal (for example a visual signal, an audio signal and/or a vibration signal).

Preferably, the inventive method is at least partly executed by a computer. That is, all steps or just some of the steps (i.e. less than a total number of steps) of the inventive method may be executed by a computer.

The inventive method preferably is a data processing method of determining a trajectory of a medical instrument to be inserted into a patient's body for treatment of a target region in the patient's body. The medical instrument preferably is configured to supply a medical substance, in particular a fluid (fluid drug or contrast agent) to the target region and is embodied in particular by a fluid line such as a catheter or a cannula (in particular a syringe needle). The data processing method is embodied in particular by a planning method of planning the trajectory. Preferably, medical image data comprising medical image information is acquired as a step of the inventive method. The medical image information in particular describes, in particular represents, an image of an anatomical body part of the patient. The anatomical body part in particular is or comprises a target region. Within the framework of this disclosure, a target region is understood to be a region in the patient's body which shall be treated in particular by application of a medical substance, and therefore constitutes a region which shall be subjected to in particular the treatment effects of a drug or the contrast-enhancing effects of a contrast agent. Other regions of the anatomical body part represent in particular off-target regions (which at the same time do not belong to the target region). Examples of off-target regions are organs at risk which shall not be subjected to the effects of the medical substance in order to avoid a detrimental outcome of the medical procedure, in particular to avoid damage to tissue which may result in for example neurological defects. Other examples for off-target regions which shall not be affected by the medical procedure such as for example eloquent regions of the brain, fibre tracts, vessels for body fluids are a cerebrospinal fluid or blood, and resection cavities arising from previous tumour therapies, from which a minimum safety distance of the trajectory should be kept. Even further examples of off-target regions include other risk objects such as the crossing of the aforementioned off-target regions, e.g. sulci, the brain midline and other structures in the patient's body which may serve as a guidance for the medical fluid and thus for spreading the medical fluid to undesired places in the body.

The medical image data preferably is generated outside of the inventive method by application of one of the aforementioned medical imaging methods to the anatomical body part. The medical image data is then preferably stored in particular on a non-volatile digital storage medium from which it then is preferably acquired by the inventive method. Alternatively or additionally, generating the medical image data may be part of the inventive method and the medical image data may be acquired online by the inventive method (i.e. within the inventive method).

Preferably, target region extent data comprising target region extent information is acquired. The target region extent information describes, in particular represents, a spatial extent of the target region in the medical image information. The spatial extent of the target region is defined in particular as a number of image particles, which are in particular discrete and are represented by for example pixels or voxels or other discrete units which may be applied for discretizing and in particular displaying the medical image information. The spatial extent of the target region therefore is to be understood as its size in terms of image particles rather than defining its physical size within the patient's body. The spatial extent of the target region preferably is defined in the dimensionality applied for processing the medical image information, in particular in the dimensionality used for displaying it, such as in three dimensions or two dimensions.

Preferably, it is determined, based on the target region extent data (in particular, on the target region extent information), whether the spatial extent of the target region in medical image information comprises more than one image particle. To this end, the target region is determined, in particular outlined, by classifying tissue types represented by the medical image information. The target region can then be defined as being constituted of one or more tissue types. The target region extent data then is preferably acquired on this basis. The classification of tissue types is effected in particular automatically, for example by running an image segmentation algorithm on the medical image data, or by user input of a corresponding attribute of the at least one image particular, in particular by manually delineating the target region by user interaction using for example a pointer tool for classifying, the tissue types in particular by marking the outer boundary of the target region in the medical image information. According to one embodiment of the invention, these two alternatives may also be applied in combination. Applying an image segmentation algorithm to the medical image information is an embodiment of automatically processing the medical image data in order to classify the tissue types. The inventive method then preferably continues with counting the image particles contained in the thus determined target region and to thus determine the spatial extent of the target region.

If it is then determined that the target region comprises more than a predetermined number of image particles, in particular more than one image particle, the inventive method preferably continues with determining, based on the medical image data (in particular, based on the medical image information), image particle weight data. The image particle weight data in particular comprises image particle weight information which describes, in particular represents, preferably a weight assigned to each target region image particle. A target region image particle is understood to be an image particle contained in the target region as described above, thus being part of (lying in) the spatial extent of the target region. For example, the colour value of each target region image particle is determined. A target region may comprise or be, for example, a tumour, a fiber track or edema. Weighting of each image particle may be based on for example adding up a numeric value assigned to each of those types of target region. In particular, an image particle may be located in more than one of those types of target region. For example an image particle lying just in a tumour may be assigned a value of 1, an image particle lying in both a tumour and edema may be assigned a value of 2, and an image particle lying in all three of tumour, edema and fiber track may be assigned a value of 3. These numeric values represent the weight which is assigned as image particle weight information. These weights may then be color coded to visually indicate "hot spots" that should be targeted by the envisaged medical procedure.

The colour values determined thereby are then preferably compared to predetermined colour values which in a predetermined database are associated with specific tissue types. The different tissue types contained in the target region may then be identified in the medical image information and the target region may thus be divided into components which comprise, in particular consist of, the specific individual tissue types. These components of the target region are also termed tissue type components.

Preferably, the weight to be assigned to each target region image particle describes the tissue type component, more specifically the tissue type contained in the tissue type component. The tissue type component is represented at least partly by the image particle to which the weight is assigned, i.e. that image particle is contained in the part of the target region representing the respective tissue type component. Preferably, assigning the weights includes assigning a numeric value to each target region image particle. In particular, the weight is represented by a numeric value. The tissue type components represent tissue types contained in the target region. If the target region represents a tumour, the tissue type components for example represent at least one of edema, an enhancing or non-enhancing tumour, fibre tracks, a two centimetre margin around the tumour, and the tumour core. Additionally, the tissue type components may represent off-target regions, in particular objects at risk such as sulci, vessels for blood or other body fluids such as for example cerebrospinal fluid, or organs at risk such as eloquent regions of the brain, the heart or the liver. An image segmentation algorithm may for example determine the different tissue type based on PET/SPECT-perfusion or diffusion tensor imaging (DTI)/ADC (apparent diffusion coefficient) values or FA (fractional anisotropy) maps. Based on such values, the inventive method is capable of determining where for example a tumour is most active and where there are necrotic regions in particular by discerning between hard and fluid-filled tissue. The numeric value representing the weight preferably increases with the proximity of the image particle to which it is assigned to the centre of the target region, in particular to the centre of a tumour.

Preferably, each tissue type component is defined as a closed area, in particular a two-dimensional closed surface (in particular circular surface) or three-dimensional volume, in particular closed volume, more particularly closed spherical volume, in the medical image information. In general, however, the tissue type components are defined as areas (i.e. surface or volumes) having an irregular shape. The surface or volume, respectively, comprises a finite number of at least one target region image particle. In general, however, the surface or volume will comprise a plurality of target region image particles. A closed surface or closed volume, respectively, in the framework of this disclosure is understood to define a surface or volume, respectively, which does not have any two- or three-dimensional discontinuities such as boundaries (in particular, open or free boundaries) or openings in its interior. In particular, the two-dimensional closed surface is represented by a disk rather than a ring and a three-dimensional volume is represented by a full sphere rather than a hollow sphere. Due to such a geometry of a closed surface or closed volume, respectively, the tissue type components may overlap, in particular specific tissue type components may be located completely inside other tissue type components, and in particular may be surrounded by, other tissue type components. A tissue type component being surrounded by another tissue type component may also be termed "inner tissue component". Preferably, the weight assigned to a target region image particle depends on, in particular increases with, the number of tissue type components which are assigned to the target region image particle. In particular, the weight depends on, more particularly increases with, the number of surfaces or volumes in which the target region image particle is contained (i.e. of which it is a member), in particular in which the target region image particle is located or by which it is surrounded. Further preferably, an individual weight is assigned to each target region image particle for each tissue type component which is assigned to it, in particular for each surface or volume of which the target region image particle region is a member. Preferably, a sum of those weights is then assigned to the target region image particle. That sum in particular is unique in the sense that it uniquely defines the combination of tissue type components of which the target region image particle is a member. The predetermined weights for each tissue type are chosen accordingly so that no sum of weights can lead to the same sum for different combinations of tissue types. The sum therefore represents the specific combination of tissue types, in particular of tissue component surfaces or tissue component volumes, of which the target region image particle is a member.

This way of defining tissue type components as closed surfaces or closed volumes and adding the weights assigned to each target region image particle supports determining those target region image particles which have the highest sum of weights and therefore with a specific probability are a member of, i.e. lie within, the most tissue type components. Those target region image particles may then be chosen as a reduced target region in the sense that they represent a reduced target region for the purpose of determining a target end point of the trajectory along which the instrument is to be introduced.

Preferably, instrument trajectory data comprising instrument trajectory information is determined based on the image particle weight data and the medical image data (in particular, based on the image particle weight information and the medical image information). The instrument trajectory information describes, in particular represents, a trajectory of the medical instrument along which the instrument is to be inserted into the patient's body. Preferably, the trajectory is a straight line curve having an entry point at which the medical instrument is to be inserted into the patient's body. Therefore, determining the instrument trajectory data preferably comprises determining that entry point. The target end point of the trajectory is preferably determined as described above. The entry point is preferably defined to lie on the surface of a trajectory volume including all possible in particular straight line trajectories from any possible entry point towards the target region. The target region, in particular the reduced target region, is also located inside the trajectory volume and is used as a boundary condition for determining the target-side end (target end point) of the trajectory. In particular, the target-side end of the trajectory is set to have a predetermined distance from and direction towards (i.e. position relative to) the target region, preferably the reduced target region. The trajectory volume in particular is the volume within which the trajectory must be contained as a starting condition for optimization of the trajectory, in particular as a starting condition for determining the instrument trajectory data. In general, the locations of a number of generally possible entry points and the locations of off-target regions, in particular objects at risk, and the location of the target region (in particular, the reduced target region) are known when determining the instrument trajectory data. The trajectory is preferably determined such that it keeps a minimum distance from, in particular does not intersect, excluded regions (such as an object at risk).

The optimal trajectory is then preferably determined based on the boundary conditions which in particular depend on the medical substance to be delivered to the target region. Furthermore, the boundary conditions may also depend on the medical instrument used for that delivery. In particular, if a catheter is used as the medical instrument, there will be an expected backflow from the catheter tip. Based on predetermined knowledge of that backflow, the trajectory should be determined such that the catheter is placed in order to avoid leakage by backflow running into fluid-guiding structures such as vessels or sulci, and to maximize coverage of the target by the medical substance. For example, the catheter should be inserted deep enough such that backflow will not cross a sulcus or other epyndymal surfaces and thereby cause a leak of the medical substance. If desired, a rather contrasting boundary condition may be used, namely that the catheter tip should be placed to take advantage of the backflow in order to optimize coverage of the target by the medical substance. For example, for some drugs, fibre tracts will be an object at risk for which leakage of infusate should be avoided. For other drugs and medical procedures, fibre tracts may represent an opportunity for better distribution and coverage of the target (such as for example in the case of treating diffused tumours or treating brain diseases such as Lysosomal Storage Diseases, Alzheimer's disease or neurodegenerive diseases in general).

The instrument trajectory data is preferably determined by automatically running a large number of simulations for potential trajectories and optimally matching the resulting volumes of distribution of the medical substance to the target region in order to identify the optimal trajectory while avoiding a crossing of objects at risk by the trajectory, in particular by the medical instrument. The optimal trajectory may then be determined automatically or by user input. For example, a user may select the optimal trajectory from a number of determined trajectories which are preferably automatically ranked according their suitability for the envisaged procedure.

The invention is furthermore directed to a system for an image-guided medical procedure, in particular image-guided drug-based tumour therapy. The system preferably comprises a computer such as the computer described above which is configured to execute a program as defined above for performing the method steps in accordance with the above-described method. The computer is in particular configured to process the medical image data, the target region extend data, the image particle weight data and the instrument trajectory data and in particular the information content of each of these kinds of data. The system further preferably comprises a detection device for detecting the position of the medical instrument, the detection device comprising in particular an analytical device for generating the medical image data, in particular at least one of an X-ray device and a computed tomography device working on the principles of X-ray absorption or nuclear magnetic resonance. Preferably, the system comprises a data interface for receiving, in particular from the analytical device, data comprising information describing (in particular representing) the position of the medical instrument (in particular relative to the above-described anatomical body part and/or the target region) and for supplying that data to the aforementioned computer. The system preferably also comprises a user interface for receiving data (in particular, information contained in the data) from the computer in order to provide information to a user. The data received by the computer is preferably generated by the computer on the basis of the results of the processing performed by the computer, in particular on the basis of the results of data processing in accordance with the above-described method.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

It is to be noted that the invention does not comprise or encompass an invasive step representing a substantial physical intervention on the (human or animal) body which requires professional medical expertise to be carried out and which entails a substantial health risk even when carried out with the required professional care and expertise. In particular, the invention does not comprise or encompass such an invasive step in connection with acquiring the medical image data and determining the instrument trajectory data.

In the following, an example embodiment of the present invention is described with reference to a FIGURE, which are merely to be regarded as examples of the invention without limiting the invention to this specific embodiment.

Figure 1:
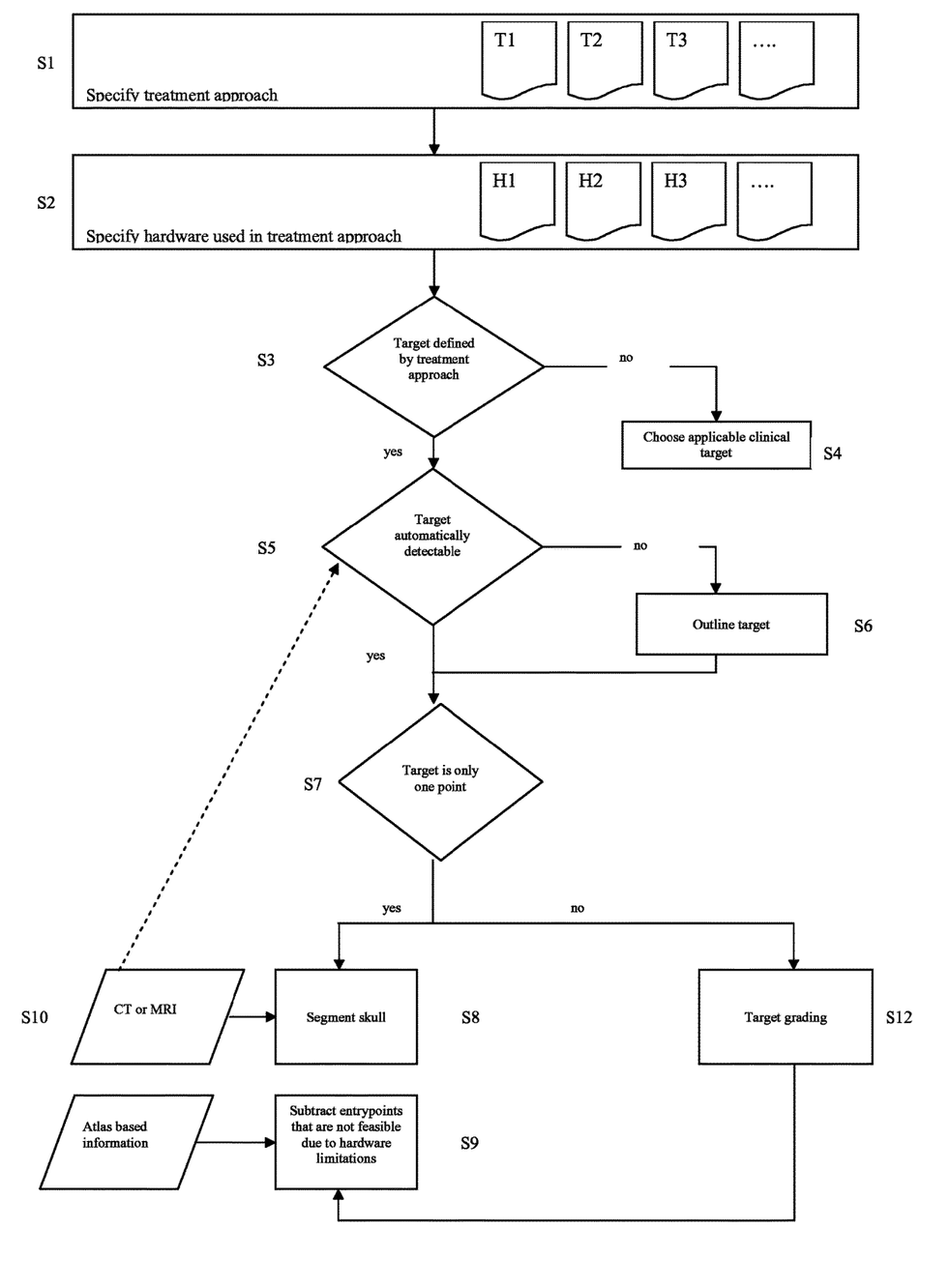
FIG. 1 shows a flow diagram of an embodiment of the above-described method of determining a trajectory, in particular planning the trajectory.

According to the flow diagram shown by FIG. 1, the inventive method starts with a step S1 in which the treatment approach for the envisaged medical procedure is specified. In particular, a treatment approach is selected from different possible treatment approaches Ti (i=1, 2, 3, . . . ) wherein each Ti represents for example at least one of drug-based tumour therapy, application of a contrast agent, a surgical procedure (for example, for removal of tumour tissue) and an endoscopic procedure for generating an in-situ image of the anatomical body part, in particular of the target region.

In step S2, the method carries on with specifying the hardware, in particular the medical instrument to be inserted into the patient's body, which is to be used in the treatment approach. The hardware is selected from possible sets of hardware Hi (i=1, 2, 3, . . . ) comprising each at least one of a catheter, a canular, a cutting or abrading instrument (for example, a scalpel or surgical scissors or pincers) and an endoscope. The hardware is specified preferably based on the information about the treatment approach, in particular the medical procedure, to be planned.

The method then continues with acquiring the medical image data and checking whether a target (target region) is defined by the treatment approach selected in step S1. If it is determined that the target is not defined by the treatment approach, an applicable clinical target (target region) is chosen (determined) in step S4. Step S4 is in particular directed to determining the target region in general anatomical terms rather than determining the location of the target region, in particular its position relative to the anatomical body part, or its spatial extent. From step S4, the method then continues to step S5.

If step S3 determines that the target region is not defined by the treatment approach specified in step S1, the method continues, from step S3, directly to step S5. Step S5 is directed to determining whether the target region is automatically detectable in the medical image data (in particular, in the medical image information). If step S5 determines that the target region is not automatically detectable, the method continues to step S6 in which the target region is outlined in the medical image information. In particular, step S6 comprises determining the location of the target region, in particular its position relative to the anatomical body part. Preferably, the target region is visually highlighted in a display of the medical image information. Outlining the target region is preferably conducted by manually delineating it by user interaction using for example a pointer tool as described above.

If step S5 determines that the target region is automatically detectable, the location of the target region, in particular the position of the target region relative to the anatomical body part, is automatically determined for example by image segmentation of the medical image data as described above. In that case, the inventive method continues directly from step S5 to step S7. Otherwise, the method continues from step S6 to step S7.

In step S7, it is determined whether the target region is only one point, i.e. the target region extent data is determined. According to an alternative embodiment, step S7 may comprise determining whether the target region in the respective display of the medical image information (in particular, in the respective resolution used for that display) comprises more than a predetermined number of image particles, in particular more than one image particle. Preferably, the medical image data is displayed with a predetermined (in particular, normalized) resolution such that the determination of step S7 is conducted based on a standard measure of spatial extent of the target region in the medical image information.

If step S7 determines a positive answer, the anatomical body part, in the case of FIG. 1 the skull, is segmented by applying an image segmentation algorithm in step S8. The image segmentation algorithm is run on the medical image data which is acquired based on an image generated with a CT or MRI tomograph as represented by step S10. The medical image data generated in step S10 may also serve as an input to step S5. If the answer to step S7 is positive, the method continues further to step S9 for determining feasible entry points for the medical instrument into the patient's body, the target end point of the trajectory of the medical instrument being fixed by the target region being of predetermined size, in particular comprising only one point (one image particle). The entry points for the medical instrument, i.e. the entry end point of the trajectory of the medical instrument, is determined in particular by subtracting non-feasible entry points from the overall number of general possible entry points, which non-feasible entry points are not feasible due to hardware limitations imposed in particular by the medical instrument, such as its flexibility, geometric size and health dangers imposed by its use.

The set of generally possible entry points is acquired in particular from atlas-based information (which is acquired in step S11). An atlas typically consists of a plurality of generic models of objects, wherein the generic models of the objects together form a complex structure. The atlas of a femur, for example, can comprise the head, the neck, the body, the greater trochanter, the lesser trochanter and the lower extremity as objects which make up the complete structure. The atlas of the brain, for example, can comprise the telencephalon, the cerebellum, the diencephalon, the pons, the mesencephalon and the medulla as the objects which make up the complex structure. One application of such an atlas is in the segmentation of the medical images, wherein the atlas is matched to medical image data, and the image data is compared to the matched atlas in order to assign a point (i.e. an image particle such as a pixel or a voxel) of the image data to an object of the matched atlas, thereby segmenting the image data into two objects.

By defining the target end point of the trajectory based on a positive answer to step S7 and the entry end point of the trajectory in step S9, both end points of the trajectory are determined. It is generally assumed that the trajectory is a straight line, whereby the entire trajectory is determined by the entry point and the target end point. According to a further embodiment of the invention, in particular step S9 may comprise determining feasible entry end points also based on the boundary condition that the trajectory shall not intersect specific off-target regions, in particular objects at risk.

If it is determined in step S7 that the target region comprises more than a predetermined number of particles, in particular more than only one image particle (point), the method continues to step S12 for target region grading which involves the above-described determination of the image particle weight data and of tissue-type components in order to determine a reduced (narrowed-down) target region. Thereby, the core of the target region may be determined in order to have a focused target end point of the trajectory. Thereby, the target end point of the trajectory may be determined with higher precision than without the target region grading (target grading). The inventive method then continues to step S9 for determining the entry end points as described above with regard to step S9 and S11.

The invention claimed is:

1. A method of determining a trajectory of a medical instrument to be inserted into a patient's body for treatment of a target region in the patient's body, the method being executed by a computer and comprising the following steps:
   a) acquiring medical image data comprising medical image information representing an image of an anatomical body part;
   b) acquiring target region extent data comprising target region extent information describing a spatial extent of the target region in the medical image information, the spatial extent being defined as a number of image particles comprised in the target region called target region image particles, an image particle being a discrete unit for displaying the medical image information;
   c) determining, based on the target region extent data, whether the spatial extent of the target region in the medical image information comprises more than one image particle;
   d) determining, based on the medical image data, image particle weight data comprising image particle weight information describing a weight represented by a numeric value describing a tissue type component of the target region, which numeric value is assigned to each target region image particle in the target region and depends on the number of tissue type components assigned to the respective image particle, which component is represented at least partly by the image particle; and e) determining, based on the image particle weight data and the medical image data, instrument trajectory data comprising instrument trajectory information describing a trajectory of the medical instrument along which the instrument is to be inserted into the patient's body, wherein determining the instrument trajectory data comprises determining an entry point at which the medical instrument is to be inserted into the patient's body, wherein the entry point is defined to lie on a surface of a trajectory volume defined by all possible trajectories from any possible entry point towards the target region, wherein an individual weight is assigned to each target region image particle for each tissue type component assigned to it, and a unique sum of those weights is assigned to the target region image particle, the sum representing the specific combination of tissue types, wherein the instrument trajectory data is determined based on that sum, and wherein a target end point of the trajectory is determined to lie in a reduced target region comprising the target region image particles having a highest sum of weights.

2. The method according to claim 1, wherein each tissue type component is defined as a two-dimensional closed surface or three-dimensional volume in the medical image information.

3. The method according to claim 1, wherein the target region extent data is acquired based on at least one classification of tissue types represented by the medical image information or user input indicating at least one image particle in the medical image information as being part of the target region.

4. The method according to claim 3, wherein the classification of tissue types is done by applying an image segmentation algorithm to the medical image data, and wherein the at least one image particle is determined as being part of the target region based on received user input indicating a corresponding attribute to the at least one image particle.

5. The method according to claim 1, wherein the tissue type components represent at least one of edema, an enhancing or non-enhancing tumour, fibre tracts, a 2 cm margin around a tumour, sulci, or vessels for blood.

6. The method according to claim 1, wherein the instrument trajectory data is determined under a boundary condition that the trajectory described by the instrument trajectory information does not run through an excluded region.

7. The method according to claim 1, wherein the medical instrument is configured to supply a medical substance to the target region, wherein the medical instrument in particular is or comprises a catheter or a cannula.

8. The method according to claim 1, wherein the weight depends on the number of surfaces or volumes of which the target region image is a member.

9. The method according to claim 1, wherein the weight depends on the number of surfaces or volumes in which the target region image particle is located or by which it is surrounded.

10. A non-transitory computer readable storage medium storing computer-executable instructions for a computer program which, when running on a computer or when loaded onto a computer, causes the computer to determine a trajectory of a medical instrument to be inserted into a patient's body for treatment of a target region in the patient's body, the instructions cause the computer to:

a) acquire medical image data comprising medical image information representing an image of an anatomical body part;

b) acquire target region extent data comprising target region extent information describing a spatial extent of the target region in the medical image information, the spatial extent being defined as a number of image particles comprised in the target region called target region image particles, an image particle being a discrete unit for displaying the medical image information;

c) determine, based on the target region extent data, whether the spatial extent of the target region in the medical image information comprises more than one image particle;

d) determine, based on the medical image data, image particle weight data comprising image particle weight information describing a weight represented by a numeric value describing a tissue type component of the target region, which numeric value is assigned to each target region image particle in the target region and depends on the number of tissue type components assigned to the respective image particle, which component is represented at least partly by the image particle; and e) determine, based on the image particle weight data and the medical image data, instrument trajectory data comprising instrument trajectory information describing a trajectory of the medical instrument along which the instrument is to be inserted into the patient's body, wherein, to determine the instrument trajectory data, the instructions cause the computer to determine an entry point at which the medical instrument is to be inserted into the patient's body, wherein the entry point is defined to lie on a surface of a trajectory volume including all possible trajectories from any possible entry point towards the target region.

wherein an individual weight is assigned to each target region image particle for each tissue type component assigned to it, and a unique sum of those weights is assigned to the target region image particle, the sum representing the specific combination of tissue types, wherein the instrument trajectory data is determined based on that sum, and wherein a target end point of the trajectory is determined to lie in a reduced target region comprising the target region image particles having a highest sum of weights.

11. A system for an image-guided medical procedure, comprising:

a computer comprising a non-transitory computer readable medium with a computer program, the computer configured to execute computer-executable instructions of the computer program stored on the non-transitory computer-readable storage medium to determine a trajectory of a medical instrument to be inserted into a patient's body for treatment of a target region in the patient's body, the instructions cause the computer to:

a) acquire medical image data comprising medical image information representing an image of an anatomical body part;

b) acquire target region extent data comprising target region extent information describing a spatial extent of the target region in the medical image information, the spatial extent being defined as a number of image particles comprised in the target region called target region image particles, an image particle being a discrete unit for displaying the medical image information;

c) determine, based on the target region extent data, whether the spatial extent of the target region in the medical image information comprises more than one image particle;

d) determine, based on the medical image data, image particle weight data comprising image particle weight information describing a weight represented by a numeric value describing a tissue type component of the target region, which numeric value is assigned to each target region image particle in the target region and depends on the number of tissue type components assigned to the respective image particle, which component is represented at least partly by the image particle; and e) determine, based on the image particle weight data and the medical image data, instrument trajectory data comprising instrument trajectory information describing a trajectory of the medical instrument along which the instrument is to be inserted into the patient's body, wherein to determine the instrument trajectory data comprises determining an entry point at which the medical instrument is to be inserted into the patient's body, wherein the entry point is defined to lie on a surface of a trajectory volume defined by all possible trajectories from any possible entry point towards the target region, wherein an individual weight is assigned to each target region image particle for each tissue type component assigned to it, and a unique sum of those weights is assigned to the target region image particle, the sum representing the specific combination of tissue types, wherein the instrument trajectory data is determined based on that sum, and wherein a target end point of the trajectory is determined to lie in a reduced target region comprising the target region image particles having a highest sum of weights;

a detection device for detecting the position of the medical instrument comprising an analytical device for generating the medical image data, in particular at least one of an X-ray device and a computed tomography device working on the principles of X-ray absorption or nuclear magnetic resonance;

a data interface for receiving, from the analytical device, data comprising information describing the position of the medical instrument and for supplying that data to the computer; and, a user interface for receiving data from the computer in order to provide information to a user, wherein the received data are generated by the computer on the basis of the results of the processing performed by the computer.

* * * * *